United States Patent

Mikitenko et al.

[11] Patent Number: 6,054,630
[45] Date of Patent: Apr. 25, 2000

[54] APPARATUS COMPRISING A CATALYTIC DISTILLATION ZONE COMPRISING A REACTION ZONE WITH DISTRIBUTION OF HYDROGEN

[75] Inventors: Paul Mikitenko, Noisy Le Roy; Christine Travers, Rueil Malmaison; Jean Cosyns, Maule; Charles Cameron, Paris; Jean-Luc Nocca, Rueil Malmaison; Francoise Montecot, Les Clayes Sous Bois; Jean-Charles Viltard, Valence; Michel Dorbon, Lyons; Blaise Didillon, Rueil Malmaison, all of France

[73] Assignee: Institut Francais Du Petrole, Rueil-Malmaison Cedex, France

[21] Appl. No.: 09/158,453

[22] Filed: Sep. 22, 1998

Related U.S. Application Data

[62] Division of application No. 08/774,841, Dec. 27, 1996, Pat. No. 9,888,355.

[30] Foreign Application Priority Data

Dec. 27, 1995 [FR] France .................................. 95 15530

[51] Int. Cl.⁷ .................................. C07C 5/23; C07C 5/13
[52] U.S. Cl. .......................... 585/670; 585/259; 585/671
[58] Field of Search ...................................... 585/670, 671, 585/259

[56] References Cited

U.S. PATENT DOCUMENTS

| | | | |
|---|---|---|---|
| 5,087,780 | 2/1992 | Argenbright | 585/259 |
| 5,368,691 | 11/1994 | Asselineau et al. | 203/29 |
| 5,776,320 | 7/1998 | Marion et al. | 203/29 |

*Primary Examiner*—Bekir L. Yildirim
*Attorney, Agent, or Firm*—Millen, White, Zelano & Branigan, P.C.

[57] ABSTRACT

For the treatment of a feed comprising a major portion of olefinic hydrocarbons containing 4 carbon atoms per molecule, including isobutene, 1-butene and 2-butenes in a ratio which substantially corresponds to the thermodynamic equilibrium, in which the feed is treated in a distillation zone comprising a stripping zone and a rectification zone associated with at least one hydroisomerization reaction zone, the hydroisomerization reaction zone being at least partially internal to the distillation zone and comprising at least one catalytic bed, in which hydroisomerization of at least a portion of 1-butene is carried out in the presence of a hydroisomerization catalyst and at least one gas stream comprising hydrogen, such that an effluent rich in isobutene leaves the distillation zone overhead and an effluent rich in 2-butenes leaves the bottom, the process being characterized in that each catalytic bed in the internal portion of the hydroisomerization zone is traversed by an ascending co-current of the gas stream and liquid and is substantially out of contact with the distillation vapor.

12 Claims, 1 Drawing Sheet

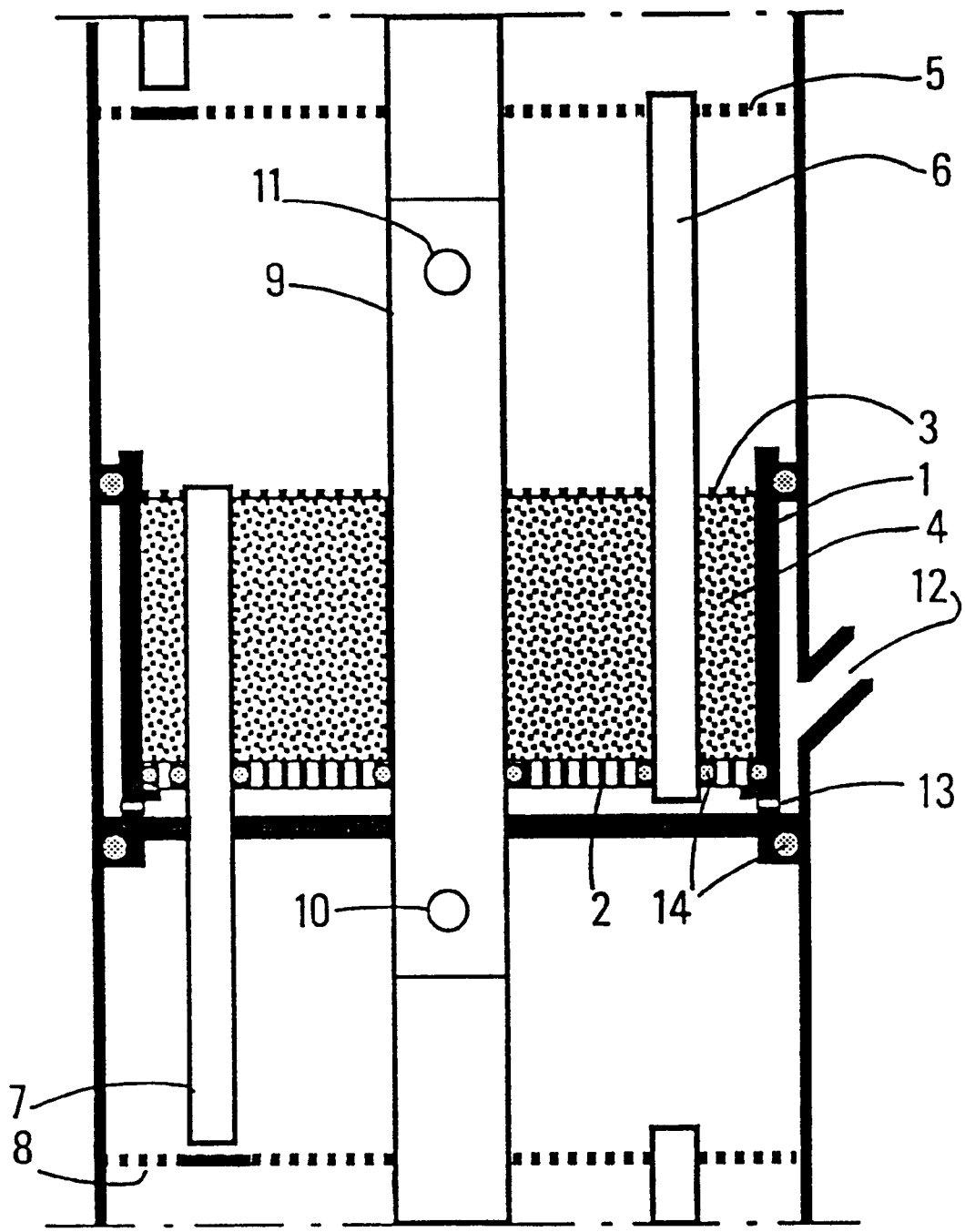

APPARATUS COMPRISING A CATALYTIC DISTILLATION ZONE COMPRISING A REACTION ZONE WITH DISTRIBUTION OF HYDROGEN

This is a division of application Ser. No. 08/774,841 filed Dec. 27, 1996 now U.S. Pat. No. 5,888,355.

FIELD OF THE INVENTION

This invention concerns the hydroisomerisation of at least a portion of the 1-butene contained in a feed, the major portion of which is constituted by olefinic hydrocarbons, including isobutene, also 1-butene and 2-butenes in a ratio which substantially corresponds to the thermodynamic equilibrium.

BACKGROUND OF THE INVENTION

This disclosure also describes apparatus and a hydrogenation process which are subjects of related applications. The apparatus of the invention can be applied to various catalytic reactions, which may be equilibrated or complete, in which at least one of the products of the reaction can be separated in a pure or diluted state by distillation under temperature and pressure conditions which are close to those of the reaction, and more particularly to paraffin isomerisation reactions involving reorganisation of the backbone, olefin isomerisation by displacement of the double bond (hydroisomerisation) or by reorganisation of the backbone, hydrogenation of unsaturated compounds to saturated compounds, dehydrogenation of saturated compounds to unsaturated compounds, and any reaction which requires the presence of hydrogen.

The hydrogenation catalyst can be disposed in the reaction zone using the different techniques proposed for carrying out catalytic distillation. These techniques have principally been developed for etherification reactions, which involve contact between the reactants in a homogeneous liquid phase and the solid catalyst. They are essentially of two types. In the first type of technique, the reaction and the distillation proceed simultaneously in the same physical space, as taught, for example, in International patent application WO-A-90/02603, U.S. Pat. Nos. 4,471,154, 4,475,005, 4,215,011, 4,307,254, 4,336,407, 4,439,350, 5,189,001, 5,266,546, 5,073,236, 5,215,011, 5,275,790, 5,338,517, 5,308,592, 5,236,663, 5,338,518 and European patents EP-B1-0 008 860, EP-B1-0 448 884, EP-B1-0 396 650 and EP-B 1-0 494 550, also European patent application EP-A1-0 559 511. In general, then, the catalyst is in contact with a descending liquid phase generated by the reflux introduced at the top of the distillation zone, and with an ascending vapour phase generated by the reboiling vapour introduced at the bottom of the zone. In the second type, the catalyst is generally disposed so that the reaction and distillation proceed independently and consecutively as taught, for example, in U.S. Pat. No. 4,847,430, U.S. Pat. No. 5,130,102 and U.S. Pat. No. 5,368,691, the vapour from the distillation step not in practice traversing any catalytic bed in the reaction zone.

For every chemical reaction requiring the addition of a foreign gaseous reactant to the distillation feed, this reactant must be introduced into the reaction zone in a different manner depending on the type of technique selected to carry out the catalytic distillation. In the first type, the gaseous reactant can simply be added to the distillation vapour at any level, but always before penetration into the reaction zone, generally substantially at the inlet to at least one catalytic bed of the reaction zone. In the second type, the gaseous reactant must be introduced in a manner appropriate to the options selected to impose a circulation direction on the liquid and gas in the catalyst bed.

It thus appears that, for a reaction which is carried out in the presence of a solid catalyst between a liquid phase reactant and a gaseous reactant which is only slightly soluble in the liquid, such as the hydrogenation of unsaturated hydrocarbons mixed with other hydrocarbons, the option which consists of carrying out catalytic distillation by avoiding passing the distillation vapour over the catalyst and causing the liquid and the gaseous reactant to circulate in an ascending co-current in the catalytic bed is the most efficient. It appears that the pressure drop across the catalytic bed(s) in the first type does not produce an intimate mixture of the liquid and gas stream containing hydrogen. In effect, in that type of technique, where the reaction and the distillation proceed simultaneously in the same physical space, the liquid descends through the catalytic bed in rivulets, i.e., in streams of liquid. The gaseous fraction containing the vaporised fraction of the feed and the gas stream containing hydrogen ascend through the catalytic bed in columns of gas. In this disposition, the entropy of the system is greater and the pressure drop across the catalytic bed(s) is lower. Thus operating in accordance with the first type does not encourage dissolution of hydrogen in the liquid phase comprising the unsaturated compound(s).

The second type, comprising a specific apparatus for distributing the liquid fraction to be hydrogenated and the gas stream comprising hydrogen, where said liquid fraction and said gas stream traverse the catalytic bed in an ascending co-current, can effect the hydrogenation reaction essentially in the absence of the gaseous fraction of the feed and under conditions under which the pressure drop across the catalytic bed(s) is the greatest. Increasing the pressure drop because of the specific apparatus of the invention can increase the solubility of the hydrogen in the liquid phase and can thus encourage hydrogenation in the liquid fraction.

In addition, because of the recognised toxicity of benzene and olefins, which are unsaturated compounds, the general tendency is to reduce the amount of these constituents in gasoline. Benzene has cancer-causing properties and thus any possibility of it polluting the ambient air has to be limited as much as possible, particularly by practically excluding it from automobile fuels. In the United States, reformulated gasoline cannot contain more than 1% of benzene; in Europe, while the restrictions are not yet as severe, it has been recommended that this value be slowly approached. Further, olefins have been recognised as being among the most reactive hydrocarbons in the cycle of photochemical reactions with oxides of nitrogen, which occur in the atmosphere and which lead to the formation of ozone. An increase in the ozone concentration in air may be a source of respiratory problems. A reduction in the amount of olefins contained in gasoline, in particular the lightest olefins which have the greatest tendency to volatilise during manipulation of the gasoline, is thus desirable.

The benzene content of a gasoline is largely dependent on that of the reformat component of that gasoline. The reformat results from catalytic treatment of naphtha for the production of aromatic hydrocarbons which principally contains 6 to 9 carbon atoms per molecule and in which the very high octane number provides the gasoline with antiknock properties. Because of the toxicity described above, it is thus necessary to reduce the benzene content of the reformat by as much as possible. A number of methods can be envisaged.

The first method consists of limiting the amount of benzene precursors such as cyclohexane and methylcyclopentane in the naphtha constituting the feed to a catalytic reforming unit. This solution substantially reduces the benzene content in the effluent from the reforming unit but is not sufficient in itself when the content must be reduced to as low as 1%. A second method consists of eliminating a light fraction of the reformat containing benzene by distillation. This solution produces a loss of the order of 15% to 20% of hydrocarbons which could be used in the gasoline. A third method consists of extracting the benzene present in the effluent from a reforming unit. A number of techniques can, in principle, be applied: solvent extraction, extractive distillation, adsorption, None of these techniques can be applied on an industrial scale, as none of them can selectively extract benzene in an economical manner. A fourth method consists of chemically transforming the benzene to convert it to a constituent which does not suffer legal limits. Alkylation by ethylene, for example, transforms the benzene to mainly ethylbenzene. This operation, however, is expensive because of the occurrence of secondary reactions which necessitate separation steps which use a great deal of energy.

Benzene of a reformat can also be hydrogenated to cyclohexane. As it is impossible to selectively hydrogenate benzene in a mixture of hydrocarbons which also contains toluene and xylenes, it is thus necessary first to fractionate the mixture to isolate a cut which contains only benzene, which can then be hydrogenated. A process has also been described in which the benzene hydrogenation catalyst is included in the rectification zone of a distillation column which separates benzene from other aromatics (Benzene Reduction—Kerry Rock and Gary Gildert, CDTECH—1994—Conference on Clean Air Act Implementation and Reformulated Gasoline—October 1994), which can save on apparatus.

Further, isobutene for polymerisation must be more than 99% pure and can only contain traces of 1-butene and 2-butenes (several tens of parts per million by weight, ppm). If the amount of impurities in the isobutene is too high, the polymers obtained are of poorer quality and the polymerisation yield is lower. Thus other olefinic hydrocarbons containing 4 carbon atoms per molecule must be eliminated from a hydrocarbon cut containing isobutene. 1-butene and isobutene have very close boiling points. Separation by distillation is only possible using drastic measures. The other olefinic hydrocarbons containing 4 carbon atoms can be separated from the isobutene by distillation. The principal problem in the production of high purity isobutene is thus separation of 1-butene from isobutene. A number of methods can be used to carry out such a separation.

The first method consists of extraction using sulphuric acid: isobutene is selectively hydrated and then regenerated by treating the aqueous phase. If the temperature and concentration are controlled properly, such a process can produce isobutene with high purity. However, the yield normally does not exceed 90%, extraction is not complete and dimers and oligomers are formed which lead to the formation of toxic acid sludge. The second method consists of cracking the methyl ether of tertio-butyl alcohol (MTBE): isobutene is extracted from the $C_4$ cut by reacting it with methanol to form MTBE. The MTBE is then cracked to methanol and isobutene on an acid catalyst. The yield can be at least 96%. The isobutene produced is of high purity but the dimethylether which can be formed during cracking must be removed. The third possible method is dehydration of tertiary butyl alcohol (TBA). In the preceding operation, the methanol can be replaced by water, leading to the production of TBA. Isobutene is then recovered by dehydration of the TBA. This method is practically never used, primarily because TBA is closely linked to the propylene oxide market. Using those processes, TBA can be a by-product of propylene oxide.

U.S. Pat. No. 2,403,672 describes a process for the separation of isobutene from a mixture of isobutene and 1-butene which comprises introducing the mixture into an isomerisation and fractionation zone in which the isomerisation catalyst also acts as a packing which carries out the distillation function. This solution has the major disadvantage of not having good distillation efficiency and thus has a mediocre capacity for separating the isobutene from the 1-butene. In this technique, the reaction and distillation proceed simultaneously in the same physical space. The catalyst is in contact with a descending liquid phase generated by the reflux introduced at the top of the distillation zone, and with an ascending vapour phase generated by the reboil vapour introduced to the bottom of the zone.

The invention concerns a reactive distillation apparatus comprising a distillation zone which comprises a stripping zone and a rectification zone associated with a reaction zone, at least a portion of which is internal to said distillation zone, and comprising at least one catalytic bed in which a feed is transformed in the presence of a catalyst and at least one gas stream comprising hydrogen, said apparatus being characterized in that each catalytic bed in the internal portion of said reaction zone is traversed by an ascending co-current of said gas stream and liquid.

The apparatus of the invention generally comprises:
- at least one means for distributing the major portion of the liquid from the bottom to the top through the catalyst;
- at least one means for circulating the major portion of the distillation vapour from the bottom to the top through the catalytic bed such that said vapour is not in practice in contact with the catalyst; and
- at least one means for distributing the major portion of the gas stream from the bottom towards the top through the catalyst.

The feed supplied to the distillation zone is generally introduced into said zone to at least one level in said zone, preferably principally to a single level of said zone.

The distillation zone generally comprises at least one column provided with at least one distillation contact means selected from the group formed by plates, loose packing and structured packing, as is known to the skilled person, and is such that the total overall efficiency is generally at least 5 theoretical levels. In known cases in which operation of a single column causes problems, it is generally preferable to divide the zone so as to use at least two columns which form said zone when placed end to end, i.e., the rectification zone, possibly the reaction zone and the stripping zone are distributed over the columns. In practice, when the reaction zone is at least partially internal to the distillation zone, the rectification or stripping zone, preferably the stripping zone, is generally in at least one column which is different to the column comprising the internal portion of the reaction zone.

The means for circulating the distributing vapour from the bottom towards the top through the catalytic bed passes the reaction zone level where the catalytic bed is located, i.e., it is generally located in the catalytic bed, but it can also be located at the edge of said catalytic bed.

The reaction zone generally comprises at least one catalytic bed, preferably 2 to 6, and more preferably 2 to 4 catalytic bed(s); when at least two catalytic beds are incorporated into the reaction zone, these two beds may be separated by at least one distillation contact means.

The apparatus of the invention is generally such that the flow of liquid to be transformed is in a co-current with the gas stream comprising hydrogen and such that the distillation vapour does not in practice pass through any catalytic bed of the internal portion of the reaction zone (meaning that, in practice, said vapour is separated from said liquid), for any catalytic bed in the internal portion of the reaction zone. In all cases of this second type of technique, each catalytic bed of the portion of the reaction zone which is in the distillation zone is generally such that the gas stream comprising hydrogen and the liquid stream which will react circulates through said bed in a co-current, which is generally ascending, even if overall in the catalytic distillation zone the gas stream comprising hydrogen and the liquid stream which will react circulates in counter-current mode. Such systems generally comprise at least one apparatus for distributing liquid which can, for example, be a liquid distributor, in each catalytic bed in the internal portion of the reaction zone. Nevertheless, provided that the technologies used in the process of the invention have been designed for catalytic reactions between liquid reactants, without modification they are not suitable for a catalytic reaction in which one of the reactants, hydrogen, is in the gaseous state. For each catalytic bed of the internal portion of the reaction zone, it is thus generally necessary to add an apparatus for introducing a gas stream comprising hydrogen, using the techniques described below, for example.

Thus for each catalytic bed in the internal portion of the reaction zone, the internal portion of the reaction zone comprises at least one means for distributing liquid, generally located below said catalytic bed, and at least one means for introducing a gas stream, generally located below or in said catalytic bed, preferably in the latter case close to the liquid introduction means. In one technique, the means for introducing a gas stream into each catalytic bed is identical to the means for distributing liquid in the catalytic bed, i.e., there is a means for introducing gas into the liquid upstream of the means for distributing liquid (with respect to the direction of circulation of the liquid). In practice and in current parlance, this means that gas is injected into the liquid upstream of the liquid distribution means. In another technique, the means for introducing a gas stream is located substantially at the level of the liquid distributing means, the gas and liquid being introduced separately into the catalytic bed. In a further technique, the means for introducing a gas stream is located below or in the catalytic bed, preferably not far from the liquid distribution means.

Further, in one embodiment of the invention, the apparatus of the invention is such that the major portion of said gas stream is hydrogen, the major portion of the hydrogen, and preferably almost all thereof, originating from external the distillation zone.

The apparatus of the invention is generally such that, for the portion of the reaction zone which is internal to the distillation zone, the feed from the reaction zone is drawn off at a draw-off level and represents at least a portion, preferably the major portion, of the liquid flowing in the distillation zone, preferably flowing in the rectification zone and more preferably flowing to an intermediate level of the rectification zone, the effluent from the reaction zone being at least in part, preferably a major part, re-introduced into the distillation zone substantially in the proximity, i.e., generally substantially at the same height or just above or just below, usually at the same height or just below, i.e., located at a distance corresponding to a height which is in the range 0 to 4 theoretical plates from a draw-off, preferably from said draw-off, to ensure continuity of distillation. Thus for the portion of the reaction zone which is internal to the distillation zone, the liquid is drawn off naturally by flow in the portion of the reaction zone which is internal to the distillation zone and re-introduction of the liquid to the distillation zone also occurs naturally by flow of liquid from the portion of the reaction zone which is internal to the distillation zone.

In general, the apparatus of the invention comprises 1 to 4 draw-off(s) which supply the external portion of the reaction zone, when the reaction zone is not completely internal to the distillation zone. In general, the liquid which will react, either partially or completely, circulates first in the external portion of the reaction zone then in the internal portion of said zone. Two cases are then possible. In the first case, the external portion of the reaction zone is supplied by a single draw-off and then, if said portion comprises more than two reactors, these are disposed in series or in parallel. In the second case, which is preferred, the external portion of the reaction zone is supplied by at least two draw-offs.

In one of the preferred embodiments of the invention, the apparatus of the invention is such that the reaction zone is completely internal to the distillation zone.

In a preferred embodiment of the apparatus of the invention, the catalyst is disposed in the reaction zone as described in the basic apparatus defined in U.S. Pat. No. 5,368,691, and arranged such that each catalytic bed is supplied by the gas stream containing hydrogen, regularly distributed at its base, using one of the techniques described below, for example. Using this technique, if the distillation zone comprises a single column and if the reaction zone is completely inside said column, the catalyst comprised in each catalytic bed, which is internal to the distillation zone, is then in contact with an ascending liquid phase generated by the reflux introduced to the top of the distillation zone, and with hydrogen which circulates in the same direction as the liquid; contact with the vapour phase from distillation is avoided by passing at least one specially provided chimney through the distribution zone.

The invention also concerns a process for the treatment of a feed, a major portion of which is constituted by hydrocarbons containing at least 5 and preferably 5 to 9 carbon atoms per molecule, and comprising at least one unsaturated compound containing at most six carbon atoms per molecule including benzene, and treating said feed in a distillation zone comprising a stripping zone and a rectification zone, associated with a hydrogenation reaction zone which is at least partially internal to said distillation zone, in which at least a portion, preferably the major portion, of the unsaturated compounds containing at most six carbon atoms per molecule, i.e., containing up to and including six carbon atoms per molecule and contained in the feed are hydrogenated in the presence of a hydrogenation catalyst and at least one gas stream comprising hydrogen, preferably as the major portion, to cause an effluent which is depleted in unsaturated compounds containing at most six carbon atoms per molecule to leave overhead of the distillation zone and an effluent which is depleted in unsaturated compounds containing at most six carbon atoms per molecule to leave from the bottom of the distillation zone, characterized in that each catalytic bed of the internal portion of the hydrogenation zone is traversed by an ascending co-current of said gas stream and liquid and the catalytic bed is not in practice traversed by the distillation vapour.

The hydrogenation reaction zone at least partially hydrogenates the benzene present in the feed, generally in such a way that the concentration of benzene in the overhead effluent is at most equal to a set concentration, and said reaction zone hydrogenates at least a portion, preferably the major portion, of each unsaturated compound containing at most six carbon atoms per molecule (other than benzene) which maybe present in the feed.

The process of the invention preferably includes the use of the apparatus of the invention.

The distillation zone and the characteristics of the gas stream, the reaction zone, etc. . . . , have been described above with respect to the apparatus of the invention.

In one implementation of the process of the invention, the effluent from the bottom of the distillation zone is mixed with the overhead effluent from said zone, In this case, after any stabilisation which may be necessary, the mixture obtained is used as a fuel either directly or by incorporation of fuel fractions.

To carry out hydrogenation using the process of the invention, the theoretical molar ratio of hydrogen which is necessary for the desired conversion of benzene is 3. The quantity of hydrogen injected before or into the hydrogenation zone is optionally in excess with respect to this stoichiometry, more so when in addition to the benzene present in the feed, each unsaturated compound containing at most six carbon atoms per molecule present in the feed must be hydrogenated. If the conditions are such that there is an excess of hydrogen, the excess hydrogen can advantageously be recovered using one of the techniques described below, for example. As an example, the excess hydrogen which leaves the distillation zone overhead is recovered then injected upstream of the compression steps associated with a catalytic reforming unit, mixed with the hydrogen from said unit, said unit preferably operating at low pressure (i.e., generally at a pressure of less than 8 bars). This excess hydrogen can also be recovered then compressed and used again in the reaction zone.

The major portion, preferably almost all, of the hydrogen used in the reaction zone of the invention generally originates from external the distillation zone. It can originate from any source which produces hydrogen of at least 50% purity by volume, preferably at least 80% purity by volume and more preferably at least 90% purity by volume. As an example, hydrogen originating from catalytic reforming processes, from PSA (pressure swing adsorption), electrochemical generation, steam cracking or steam reforming can be used.

The operating conditions in the hydrogenation zone in the process of the invention are linked to the operating conditions used for distillation. Distillation is carried out at a pressure which is generally in the range 2 to 20 bars, preferably in the range 4 to 15 bars, and more preferably in the range 4 to 10 bars (1 bar=$10^5$ Pa), with a reflux ratio in the range 1 to 10, preferably in the range 3 to 6. The temperature at the head of the zone is generally in the range 40° C. to 180° C. and the temperature at the bottom of the zone is generally in the range 120° C. to 280° C. The hydrogenation reaction is carried out under conditions which are most generally intermediate between those established overhead and at the bottom of the distillation zone, at a temperature which is in the range 100° C. to 200° C., preferably in the range 120° C. to 180° C., and at a pressure which is in the range 2 to 20 bars, preferably in the range 4 to 10 bars. The liquid which is hydrogenated is supplied with hydrogen, the flow rate of which depends on the concentration of benzene in said liquid and, more generally, of the unsaturated compounds containing at most six carbon atoms per molecule in the feed from the distillation zone. It is generally at least equal to the flow rate which corresponds to the stoichiometry of the hydrogenation reactions taking place (hydrogenation of benzene and other unsaturated compounds containing at most six carbon atoms per molecule comprised in the hydrogenation feed) and at most equal to the flow rate which corresponds to 10 times the stoichiometry, preferably less than six times the stoichiometry, and more preferably less than 3 times the stoichiometry.

When the hydrogenation zone includes a portion which is external to the distillation zone, the catalyst disposed in said external portion can use any technique which is known to the skilled person, under operating conditions (temperature, pressure . . . ) which are or are not independent, preferably independent, of the operating conditions in the distillation zone. In the portion of the hydrogenation zone which is external to the distillation zone, the operating conditions are generally as follows. The pressure required for this hydrogenation step is generally in the range 1 to 60 bars absolute, preferably in the range 2 to 50 bars and more preferably in the range 5 to 35 bars. The operating temperature in the hydrogenation zone is generally in the range 100° C. to 400° C., preferably in the range 120° C. to 350° C., more preferably in the range 140° C. to 320° C. The space velocity in said hydrogenation zone, calculated with respect to the catalyst, is generally in the range 1 to 50 $h^{-1}$, more particularly in the range 1 to 30 $h^{-1}$ (volume of feed per volume of catalyst per hour). The hydrogen flow rate corresponding to the stoichiometry of the hydrogenation reactions taking place is in the range 0.5 to 10 times said stoichiometry, preferably in the range 1 to 6 times said stoichiometry and more preferably in the range 1 to 3 times said stoichiometry. However, the temperature and pressure conditions can also be within those established at the head and bottom of the distillation zone, without departing from the scope of the invention.

More generally, whatever the position of the hydrogenation zone with respect to the distillation zone, the catalyst used in the hydrogenation zone of the invention generally comprises at least one metal selected from the group formed by nickel and platinum, used as they are or preferably deposited on a support. The metal is generally in its reduced form for at least 50% by weight of its full quantity. However, any other hydrogenation catalyst which is known to the skilled person can also be used.

When platinum is used, the catalyst can advantageously contain at least one halogen in a proportion which is in the range 0.2% to 2% by weight with respect to the catalyst. Chlorine or fluorine is preferably used, or a combination of the two in a proportion which is in the range 0.2% to 1.5% with respect to the total catalyst weight. When a catalyst containing platinum is used, a catalyst is generally used in which the average size of the platinum crystallites is below $60 \times 10^{-10}$ m, preferably less than $20 \times 10^{-10}$ m and more preferably less than $10 \times 10^{-10}$ m. Further, the overall proportion of the platinum is generally in the range 0.1% to 1% with respect to the total catalyst weight, preferably in the range 0.1% to 0.6%.

When nickel is used, the proportion of nickel is in the range 5% to 70% with respect to the total weight of the catalyst, more particularly in the range 10% to 70% and preferably in the range 15% to 65%. Further, a catalyst is generally used in which the average size of the nickel crystallites is less than $100 \times 10^{-10}$ m, preferably less than $80 \times 10^{-10}$ m, and more preferably less than $60 \times 10^{-10}$ m.

The support is generally selected from the group formed by alumina, silica-aluminas, silica, zeolites, activated charcoal, clays, aluminous cements, rare earth oxides and alkaline-earth oxides, used alone or as a mixture. Preferably, a support based on alumina or silica is used, with a specific surface area which is in the range 30 to 300 $m^2/g$, preferably in the range 90 to 260 $m^2/g$.

This particularly claimed invention concerns a process for the treatment of a feed comprising, as its major portion, olefinic hydrocarbons containing 4 carbon atoms per molecule, including isobutene, also 1-butene and 2-butenes in a ratio which substantially corresponds to the thermodynamic equilibrium, in which said feed is treated in a distillation zone comprising a stripping zone and a rectification zone associated with a hydroisomerisation reaction zone, said reaction zone being at least partially internal to said distillation zone and comprising at least one catalytic bed, in which hydroisomerisation of at least a portion and preferably the major portion of 1-butene is carried out in the presence of a hydroisomerisation catalyst and a gas stream comprising hydrogen, preferably as its major portion, such that an effluent which is rich in isobutene, generally of high purity, leaves the distillation zone overhead and an effluent which is depleted in isobutene leaves the bottom, said process being characterized in that each catalytic bed in the internal portion of the hydroisomerisation zone is traversed by an ascending co-current of said gas stream and liquid and is not in practice traversed by distillation vapour. The process can be used to produce high purity isobutene.

The process of the invention preferably includes the use of the apparatus of the invention.

The feed supplied to the distillation zone is generally introduced into said zone to at least one level of said zone, preferably principally to a single level of said zone. It is in a ratio which substantially corresponds to the 1-butene/2-butenes thermodynamic equilibrium on introduction. In a preferred implementation of the process of the invention, the feed is obtained from a cut with a major portion comprised of olefinic hydrocarbons containing 4 carbon atoms per molecule, including isobutene and 1-butene, by treatment of said cut in a first hydroisomerisation zone, which is generally independent of the optional portion of the hydroisomerisation reaction zone which is external to the associated distillation zone, the major portion of the effluent from said first hydroisomerisation zone acting as the feed, which is principal or secondary according to the definitions given below in the text, which supplies the distillation zone. If the feed includes polyunsaturated compounds, usually dienes and/or acetylenes, the compounds are preferably transformed to butenes in the first hydroisomerisation zone before introduction into the distillation zone. However, any other technique which can produce a feed in which the 1-butene and 2-butenes are in a ratio which substantially corresponds to the thermodynamic equilibrium from a cut with olefin $C_4$ hydrocarbons as its major portion is also within the scope of the invention.

The first optional hydroisomerisation reaction zone located upstream of the distillation-reaction zone effects at least partial selective hydrogenation of the polyunsaturated compounds, usually dienes such as butadiene, in addition to hydroisomerisation of at least a portion of the 1-butene to 2-butenes. It generally comprises at least one catalytic hydroisomerisation bed comprising a hydroisomerisation catalyst, preferably with 1 to 4 catalytic beds; when at least two catalytic beds are incorporated into the reaction zone, these two beds are preferably distributed over at least two reactors, in series or in parallel, preferably in series. As an example, said first reaction zone comprises a single reactor containing at least one catalytic bed, preferably only one. In a preferred implementation of the process of the present invention, said first reaction zone comprises two reactors which are generally in series each comprising at least one catalytic bed, preferably only one. When the reaction zone comprises at least two reactors, any recycling of at least a portion of the effluent from at least one of the reactors in the first reaction zone to the first zone is generally made to the inlet of one reactor, preferably to said reactor, preferably before injection of the gaseous compound comprising hydrogen. It is also possible to recycle around the first zone itself, i.e., generally to the inlet of the first reactor to said zone, preferably before injection of the gaseous compound comprising hydrogen; as an example, with two reactors, at least a portion of the effluent from the second reactor is recycled to the inlet to the first reactor. This can advantageously reduce the concentration of polyunsaturated compounds in the effluent from the first reaction zone.

The operating conditions of the first hydroisomerisation zone, when present, are generally as follows: the catalyst is identical to the catalyst from the hydroisomerisation zone which will be described below. The pressure is generally in the range 4 to 40 bar (1 bar=0.1 MPa), preferably in the range 6 to 30 bar. The temperature is generally in the range 10° C. to 150° C., preferably in the range 20° C. to 100° C. The $H_2$/hydrocarbons molar ratio is generally adjusted so as to obtain practically complete conversion of the polyunsaturated compounds such as butadiene and sufficient isomerisation of 1-butene to 2-butenes with limited alkane formation.

The hydroisomerisation reaction zone associated with the distillation zone generally comprises at least one catalytic hydroisomerisation bed comprising a hydroisomerisation catalyst, preferably 2 to 4, and more preferably 2 to 6 catalytic beds; when at least two catalytic beds are incorporated into said distillation zone, these two beds are preferably separated by at least one distillation contact means. The hydroisomerisation reaction zone at least partially hydroisomerises at least a portion, preferably the major portion, of the 1-butene present in the feed to 2-butenes (cis and trans), generally such that the 1-butene concentration in the overhead effluent from the distillation zone is a maximum of a certain value.

The distillation zone used in the process of the invention is identical to that described above.

In a preferred implementation of the process of the invention, in addition to supplying the distillation zone with the principal feed, it is supplied with a secondary feed (secondary with respect to the principal feed) which may or may not originate from a hydroisomerisation reaction zone such as the first, optional, hydroisomerisation reaction zone, and may or may not be independent of the supply of principal feed to the distillation zone. The secondary feed is generally a $C_4$ cut containing at least isobutene, also 1-butene and 2-butenes in a ratio which substantially corresponds to the thermodynamic equilibrium, and generally originates from a steam cracking process such as a crude $C_4$ cut or the 1-raffinate, or from catalytic cracking; generally and preferably, the secondary feed is a $C_4$ cut which is essentially free of polyunsaturated compounds and the 1-butene content is lower than the 1-butene content in the principal feed. If the amount of unsaturated compounds in the secondary feed is high, the feed is preferably treated in a selective hydrogenation zone before its entry into the distillation zone.

When the principal feed is introduced at a single introduction level, the secondary feed is generally introduced into the distillation zone to at least one introduction level, preferably to a single introduction level, said introduction level depending on the composition of the secondary feed. Thus in a first example, the secondary feed can be very rich in isobutene and contain less than 1.5 times the 1-butene contained in the principal feed, in which case the secondary feed is preferably introduced at a single level generally located above the level at which the principal feed is introduced. In a second example, the secondary feed is practically free of 1-butene, in which case the secondary feed is preferably introduced to a single level generally located below the level at which the principal feed is introduced. It is also possible to mix the principal feed before its entry into the distillation zone with the secondary feed.

The hydroisomerisation reaction zone associated with the distillation zone generally comprises at least one catalytic hydroisomerisation bed, preferably 2 to 6 and more preferably 2 to 4 catalytic beds; when at least two catalytic beds are incorporated into the distillation zone, these two beds are optionally separated by at least one distillation contact means. The hydroisomerisation reaction zone at least partially hydroisomerises at least a portion, preferably the major portion, of the 1-butene present in the feed to 2-butenes (cis and trans), generally such that the 1-butene concentration in the overhead effluent from the distillation zone is a maximum of a pre-set value.

The process of the invention is generally such that the flow of the liquid to be hydroisomerised is in a co-current with the flow of the gas stream comprising hydrogen in each catalytic bed of the internal portion of the hydroisomerisation zone, and such that the distillation vapour does not in practice traverse any catalytic bed in the internal portion of the reaction zone (meaning that in practice, the vapour is separated from the liquid to be hydroisomerised). Each catalytic bed in the portion of the reaction zone which is internal to the distillation zone is generally such that the gas stream comprising hydrogen and the liquid stream which is to be reacted circulate in a co-current, generally ascending, across the bed, even if overall in the catalytic distillation zone, the gas stream comprising hydrogen and the liquid stream to be reacted circulate in a counter-current. Such systems generally comprise at least one liquid distribution apparatus which can, for example, be a liquid distributor, for each catalytic bed in the internal portion of the reaction zone. The distribution apparatus for the gas streams and for liquid distribution have been described above.

The process of the invention is generally such that in all parts of the hydroisomerisation reaction zone, whether internal or, optionally, external, the feed is drawn off at the height of a draw-off and represents at least a portion, preferably the major portion, of the liquid (reflux) flowing in the distillation zone, preferably flowing in the rectification zone and more preferably flowing in an intermediate level of the rectification zone, the effluent from the hydroisomerisation reaction zone being at least in part, preferably the major part, re-introduced into the distillation zone, so as to ensure continuity of distillation. For the optional portion of the reaction zone which is external of the distillation zone, re-introduction of the effluent from the distillation zone is effected substantially in the proximity, i.e., generally substantially at the same height or just above or just below, generally at the same height or just above, i.e., located at a distance corresponding to a height which is in the range 0 to 4 theoretical plates from a draw-off, preferably from said draw-off, to ensure continuity of distillation. For the portion of the reaction zone which is internal to the distillation zone, liquid (reflux) draw-off occurs naturally by flow in the portion of the reaction zone which is internal to the distillation zone, and re-introduction of the effluent to the distillation zone also occurs naturally by flow of liquid from the internal reaction zone to the distillation zone.

In general, when the hydroisomerisation zone is not completely internal to the distillation zone, the process of the invention comprises 1 to 6, preferably 2 to 4 draw-offs, which supply the external portion of the hydroisomerisation zone. In such a case, the liquid to be hydroisomerised, either partially or completely, circulates first in the external portion of the hydroisomerisation zone then in the internal portion of that zone. Two cases are then possible. In the first case, the external portion of the reaction zone is supplied by a single draw-off and thus, if said portion comprises more than two reactors, these are disposed in series or in parallel. In the second case, which is preferred, the external portion of the hydroisomerisation zone is supplied by at least two draw-offs. A portion of the external portion of the hydroisomerisation zone which is supplied by a given draw-off, if the external portion comprises at least two draw-offs, generally comprises at least one reactor, preferably a single reactor. If said portion of the external portion comprises at least two reactors, each reactor which is external to the distillation zone is generally supplied by a single draw-off, preferably associated with a single re-introduction level, said draw-off being distinct from the draw-off which supplies the other reactor(s).

In preferred implementation of the invention, the process of the invention is such that the hydrogenation zone is completely internal to the distillation zone.

The major portion of the hydrogen used for hydroisomerisation of 1-butene, preferably almost all thereof, originates from external the distillation zone. It can originate from any source which produces hydrogen in at least 50% purity by volume, preferably at least 80% purity by volume and more preferably at least 90% purity by volume. As an example, hydrogen originating from catalytic reforming processes, from PSA (pressure swing adsorption), electrochemical generation, steam cracking or steam reforming can be used.

The operating conditions in the portion of the hydroisomerisation zone internal to the distillation zone are linked to the operating conditions used for distillation. Distillation is generally carried out in a manner which minimises the quantity of isobutene in the bottom product to maximise the yield of isobutene from the process and minimise the quantity of 2-butenes and 1-butene in the overhead product to produce high purity isobutene overhead. It is carried out at a pressure which is generally in the range 2 to 30 bars, preferably in the range 4 to 15 bars, and more preferably in the range 4 to 10 bars, with a reflux ratio in the range 1 to 30, preferably in the range 5 to 20. The temperature at the head of the zone is generally in the range 0° C. to 200° C. and the temperature at the bottom of the zone is generally in the range 5° C. to 250° C. The hydroisomerisation reaction is carried out under conditions which are most generally intermediate between those established overhead and at the bottom of the distillation zone, at a temperature which is in the range 20° C. to 150° C., preferably in the range 40° C. to 80° C., and at a pressure which is in the range 2 to 30 bars, preferably in the range 4 to 15 bars, and more preferably in the range 4 to 10 bars. The liquid which is hydroisomerised is supplied with a gas stream comprising hydrogen, preferably as the major portion.

When the hydroisomerisation zone includes a portion which is external to the distillation zone, the catalyst disposed in said external portion can use any technique which is known to the skilled person, under operating conditions (temperature, pressure . . . ) which are generally independent of the operating conditions in the distillation zone. In the optional portion of the hydroisomerisation zone which is external to the distillation zone, the operating conditions are generally as follows. The pressure required for this hydroisomerisation step is generally in the range of about 1 to 40 bars absolute, preferably in the range of about 2 to 30 bars and more preferably in the range of about 4 to 25 bars. The operating temperature in the hydroisomerisation zone is generally in the range of about 20° C. to 150° C., preferably in the range of about 40° C. to 100° C., more preferably in the range of about 40° C. to 80° C. The space velocity in said hydroisomerisation zone, calculated with respect to the catalyst, is generally in the range of about 1 to 100 $h^{-1}$, more particularly in the range of about 4 to 50 $h^{-1}$ (volume of feed per volume of catalyst per hour). The corresponding hydrogen flow rate is such that the $H_2$/hydrocarbons molar ratio on entering the hydroisomerisation zone is preferably at least about $10^{-5}$. This ratio is usually about $10^{-5}$ to about 3 and often about $10^{-3}$ to about 1. However, the temperature and pressure conditions can also be in the range which is established at the head and bottom of the distillation zone, without departing from the scope of the invention.

In order to carry out hydroisomerisation using the process of the invention, the theoretical molar ratio of hydrogen necessary for the desired conversion of 1-butene in the reaction zone associated with the distillation zone is such that the $H_2$/hydrocarbons molar ratio on entering said zone is at least $10^{-5}$. This molar ratio can be optimised so that all the hydrogen is consumed in the hydroisomerisation reaction to avoid the need for a hydrogen recovery apparatus at the outlet to the reaction zone, and so that the secondary hydrogenation reactions can be minimised to maximise the isobutene yield from the process and finally, such that there is sufficient hydrogen along the whole length of the reaction zone so that the hydroisomerisation reaction of 1-butene to 2-butenes can take place. However, if these conditions are such that there is an excess of hydrogen, the excess hydrogen can advantageously be recovered using one of the techniques described above, for example. As an example, the excess hydrogen leaving the distillation zone overhead is recovered, then injected upstream of the compression stages associated with a catalytic reforming unit, mixed with the hydrogen from said unit, said unit preferably operating at low pressure (i.e., generally a pressure of less than 8 bar). This excess hydrogen can also be recovered then compressed and used again in the reaction zone.

When a portion of the hydroisomerisation zone associated with the distillation zone is external to the distillation zone, the process of the invention can isomerise a large portion of the 1-butene to 2-butenes external the distillation zone, optionally under different temperature and/or pressure conditions to those used in the column. The inlet temperature (and, respectively, the outlet temperature) at the draw-off which supplies a catalytic bed of the portion of the hydroisomerisation zone which is external to the column is preferably substantially similar, i.e., the difference is substantially less than 10° C. with respect to the temperature at the height of the draw-off (with respect to the re-introduction level). Similarly, the hydroisomerisation reaction can advantageously be carried out in the portion of the reaction zone which is external the column at a pressure which is higher than that used internal to the distillation zone. This pressure increase can thus increase dissolution of the gas stream containing hydrogen in the liquid phase containing 1-butene to be isomerised.

In such a case, the process of the invention comprises the use of a technique known as "pumparound" which consists of passing a portion, preferably the major portion, of the liquid (reflux) outside the distillation zone in an amount which is preferably a factor of more than 1, i.e., the flow rate of a catalytic bed in the external portion of the hydroisomerisation zone associated with the distillation zone, said bed being supplied at a draw-off with a portion of the liquid effluent (reflux) flowing on the distillation plate associated with said draw-off (i.e., from which said portion of liquid effluent is drawn off) and with at least a portion of the liquid corresponding to recycling the effluent from said bed just above or just below or substantially at the same level as said draw-off is more than once the flow rate of the liquid flowing on said plate, for example 1.5 times.

More generally, the catalyst used in the hydroisomerisation zone of the process of the invention generally comprises at least one metal selected from the group formed by noble metals from group VIII of the periodic classification of the elements and nickel, i.e., selected from the group formed by ruthenium, rhodium, palladium, osmium, iridium and platinum, preferably palladium, or nickel, used as it is or, preferably, deposited on a support. At least 50% by weight of the metal is generally in its reduced form. The noble metal content of the catalyst is generally about 0.01% to about 2% by weight. When nickel is used, the proportion of nickel with respect to the total catalyst weight is in the range 5% to 70%, preferably in the range 10% to 70%, and in general, a catalyst is used in which the average size of the nickel crystallites is less than 10 nm, preferably less than 8 nm, more preferably less than 6 nm. However, any other hydroisomerisation catalyst which is known to the skilled person can also be selected. Before use, the catalyst is normally treated with a sulphur compound then by hydrogen. The catalyst is generally sulphurated in situ or ex situ such that sulphur is chemisorbed onto at least a portion of the metal. The chemisorbed sulphur encourages the isomerisation of 1-butene to 2-butenes over the isobutene hydrogenation reaction and thus maximises the isobutene yield of the process.

The hydroisomerisation catalyst support is generally selected from the group formed by alumina, silica-aluminas, silica, zeolites, activated charcoal, clays, aluminous cements, rare earth oxides and alkaline-earth oxides, used alone or as a mixture. A support based on alumina or silica is preferably used, with a specific surface area which is in the range 10 to 300 $m^2/g$, preferably in the range 30 to 70 $m^2/g$.

By way of non limiting example, according to the present invention, commercial catalysts can be used, such as those sold by the company Catalysts and Chemicals under reference C-31 or those sold by the Girdler Corporation under reference G-55 or, preferably, those sold by Procatalyse under references LD-265, LD-265S, LD-267 and LD-267R.

EXAMPLES

Examples 1 and 2 show the operation of a zone for hydrogenation of unsaturated compounds comprising at most six carbon atoms per molecule, including benzene, in accordance with the invention (Example 2) and the operation of a hydrogenation zone which was not in accordance with the invention (Example 1), with a catalyst which was loosely packed on distillation plates traversed by the liquid which circulated downwardly and by a vapour which circulated upwardly in the distillation zone.

Example 1 (comparative)

A metal distillation column with a diameter of 50 mm was used, rendered adiabatic with heating envelopes in which the temperatures were regulated to produce the temperature gradient established in the column. Over a height of 4.5 m, the column comprised, from head to foot a rectification zone composed of 11 sieve plates with downcomers, a catalytic hydrogenating distillation zone and a stripping zone composed of 63 perforated plates. The catalytic hydrogenating distillation zone was constituted by three reactive plates which in this instance were sieve plates with downcomers, with the weirs raised by 3.5 cm and in which the volume between the top of the weir and the plate could be packed with catalyst. A metal screen placed at the top of the overflow acted as a filter to prevent catalyst particles from being evacuated with the liquid leaving the plate.

Each of the three cells was packed with 36 g of nickel catalyst sold by PROCATALYSE with the reference LD 746. 260 g/h of a reformat comprising essentially hydrocarbons containing at least 5 carbon atoms per molecule was introduced to the $37^{th}$ plate in the column counting from the bottom. The reformat composition is shown in Table 1. 18 Nl/h of hydrogen was also introduced to the base of each cell. The column was started by establishing a reflux ratio of 5, regulating the bottom temperature to 176° C. and the pressure at 7 bars.

At steady state, 138 g/h and 113 g/h respectively of residue and a liquid distillate were recovered. The compositions are given in Table 1. A small portion of the distillate, constituted by the lightest hydrocarbons, was evacuated from the column with excess hydrogen and was not accounted for. Analysis of the effluents led to the deduction that the degree of hydrogenation of the olefins and benzene in the feed were respectively 100% and 55% while toluene was unaffected.

Example 2: (in accordance with the invention)

The apparatus of Example 1 was used but the catalytic distillation zone was of a different design. The catalytic hydrogenating distillation zone in this instance was constituted by three catalytic distillation doublets, each doublet being itself constituted by a catalytic cell over which three perforated plates were mounted. Construction details of a catalytic cell and its disposition in the column are shown schematically in the figure. Catalytic cell 1 consists of a cylindrical container with a flat base with an external diameter which is 2 mm smaller than the internal diameter of the column. At its lower portion above the base, a screen 2 is provided which acts both as a support for the catalyst and as a distributor for the hydrogen. A catalyst retaining screen 3 is provided at the top; the height thereof can be varied. Catalyst 4 fills the entire volume between these two screens. The catalytic cell receives the liquid from upper distillation plate 5 via downcomer 6. After passing through the cell in the upward direction, the liquid is evacuated by overflowing via downcomer 7 and flows onto lower distillation plate 8. The vapour from lower plate 8 passes into the central chimney 9, which is solid with the cell, by penetrating via orifices 10 (only one shown in the figure) and leaving below upper plate 5 via orifices 11 (only one shown in the figure). Hydrogen is introduced to the base of the catalytic cell via conduit 12 then via orifices 13 (six in total) which are distributed around the periphery of the cell, in the immediate vicinity of the base. Seals 14 prevent any hydrogen from escaping prior to its arrival at the catalytic bed.

Each of the three cells was packed with 36 g of nickel catalyst sold by PROCATALYSE with the reference LD 746. 260 g/h of the same feed as that used in Example 1 was introduced to the $37^{th}$ plate in the column counting from the bottom. The reformat composition is shown in the second column of the Table. 6 Nl/h of hydrogen was introduced to the base of each cell. The column was started by establishing a reflux ratio of 5, regulating the bottom temperature to 176° C. and the pressure at 7 bars.

At steady state, 143 g/h and 106 g/h respectively of residue and a liquid distillate were recovered. The compositions are given in Table 1. A small portion of the distillate, constituted by the lightest hydrocarbons, was evacuated from the column with excess hydrogen and was not accounted for. Analysis of the effluents led to the deduction that the degree of hydrogenation of the olefins and benzene in the feed were respectively 100% and 87% while toluene was unaffected.

TABLE 1 compositions of feed and effluents in the catalytic column

| | composition, in % by weight | | | | |
|---|---|---|---|---|---|
| | | example 1 | | example 2 | |
| | feed | residue | liquid distillate | residue | liquid distillate |
| C5 and lighter | 7.65 | | 10.22 | | 7.36 |
| of which: olefins | 0.11 | | 0 | | 0 |
| C6 | 44.83 | 9.55 | 89.78 | 12.4 | 92.59 |
| of which: olefins | 0.13 | | 0 | | 0 |
| :benzene | 6.07 | 0.63 | 5.45 | 0.07 | 1.84 |
| :cyclohexane | 1.1 | 8.34 | 0.34 | 12.16 | 0.73 |
| C7: | 42.55 | 80.72 | | 78.27 | 0.05 |
| of which: toluene | 4.78 | 9.1 | | 8.87 | |
| C8 and heavier | 4.97 | 9.73 | | 9.33 | |
| olefin conversion | | | 100% | | 100% |
| benzene conversion | | | 55% | | 87% |
| hydrogen conversion | | | 15% | | 70% |

It can be seen that the process of the present invention produces better conversion of benzene and better hydrogen conversion.

Examples 3 and 4 illustrate the case of a process of the invention for treatment of a feed the major portion of which is comprised by olefinic hydrocarbons containing 4 carbon atoms per molecule, including isobutene, 1-butene and 2-butenes in a ratio which substantially corresponds to the thermodynamic equilibrium.

Example 3

Hydroisomerisation operations were carried out successively and discontinuously on a $C_4$ distillation cut. The feed was hydroisomerised a first time. The effluent from the first test was distilled: the distillation head, representing an intermediate extraction, was hydroisomerised. The hydroisomerisation effluent, representing what would be re-injected into the column, was distilled. The head from the second distillation was hydroisomerised and the effluent from this third hydroisomerisation step was distilled.

The hydroisomerisation operations were carried out in a pilot unit provided with an adiabatic reactor. The reactor was filled with 1.5 l of catalyst LD-265 from PROCATALYSE. The catalyst was sulphurated and activated in situ using the procedure recommended by the supplier of the catalyst.

Distillation operations were carried out in an adiabatic column with an internal diameter of 163 mm and a height of 10 m. the column was constituted by 4 beds which were 1.78 m high above the feed injection point, filled with a packing sold by SUIZER under the trade name M550Y and 2 beds 1 m high below the feed injection point, filled with Pall rings.

First Hydroisomerisation

The average operating conditions during the test were as follows:

Reactor temperature: 80° C.
Reactor pressure: 20 bar
Residence time: 0.25 h
$H_2$/feed molar ratio: 3

Table 2 below shows the compositions of the feed and effluent in the hydroisomerisation reactor operating under the conditions described above.

TABLE 2

|  | Feed (weight %) | Effluent (weight %) |
|---|---|---|
| <$C_4$ | 0.25 | 0.23 |
| $iC_4$ | 2.98 | 3.10 |
| $iC_4^=$ | 44.90 | 44.42 |
| $C_4^=1$ | 26.95 | 4.26 |
| $C_4^{==}1,3$ | 0.13 | 0.00 |
| $nC_4$ | 11.72 | 14.41 |
| $C_4^=2trans$ | 8.73 | 21.37 |
| Neo $C_5$ | 0.24 | 0.23 |
| Me cyclo $C_3$ | 0.06 | 0.06 |
| $C_4^=2cis$ | 4.03 | 11.92 |
| >$C_4$ | 0.01 | 0.00 |

The legend for the table and the following tables is as follows:

<$C_4$: compounds with less than 4 (4 excluded) carbon atoms per molecule (or $C_3^-$)
$iC_4$: isobutene
$iC_4^=$: isobutene
$C_4^=1$: 1-butene
$C_4^{==}1,3$: 1,3-butadiene
$nC_4$: normal butane
$C_4^=2trans$: trans 2-butene
Neo $C_5$: neopentane (or dimethylpropane)
Me cyclo $C_3$: methyl cyclopropane
$C_4^{=2}2cis$: cis 2-butene
>$C_4$: compounds containing more than 4 (4 excluded) carbon atoms per molecule (or $C_5^+$)

First Distillation

Distillation of the effluent from the above test was carried out under the following operating conditions:

Column pressure: 4 bar
Reflux ratio (R/D): 20
Feed temperature: 33° C.
Reflux temperature: 32° C.
Column head temperature: 57° C.
Column bottom temperature: 63° C.

Table 3 below shows the compositions of the feed and the overhead effluent from the distillation column operating under the conditions described above.

TABLE 3

|  | Feed (weight %) | Head (weight %) |
|---|---|---|
| <$C_4$ | 0.23 | 0.44 |
| $iC_4$ | 3.10 | 6.71 |
| $iC_4^=$ | 44.42 | 83.35 |
| $C_4^=1$ | 4.26 | 7.39 |
| $C_4^{==}1,3$ | 0.00 | 0.00 |
| $nC_4$ | 14.41 | 1.62 |
| $C_4^=2trans$ | 21.37 | 0.44 |
| Neo $C_5$ | 0.23 | — |
| Me cyclo $C_3$ | 0.06 | — |
| $C_4^=2cis$ | 11.92 | 0.05 |
| >$C_4$ | — | — |

Second Hydroisomerisation

The average operating conditions during the test were as follows:

Reactor temperature: 65° C.
Reactor pressure: 20 bar
Residence time: 0.25.h
$H_2$/feed molar ratio: 0.6

Table 4 below shows the compositions of the feed and effluent in the hydroisomerisation reactor operating under the conditions described above.

TABLE 4

|  | Feed (weight %) | Effluent (weight %) |
|---|---|---|
| <$C_4$ | 0.44 | 0.39 |
| $iC_4$ | 6.71 | 6.91 |
| $iC_4^=$ | 83.35 | 82.94 |
| $C_4^=1$ | 7.39 | 0.81 |
| $C_4^{==}1,3$ | — | — |
| $nC_4$ | 1.62 | 2.09 |
| $C_4^=2trans$ | 0.44 | 4.44 |
| Neo $C_5$ | — | — |
| Me cyclo $C_3$ | — | — |
| $C_4^=2cis$ | 0.05 | 2.42 |
| >$C_4$ | — | — |

Second Distillation

Distillation of the effluent from the above test was carried out under the following operating conditions:

Column pressure: 4 bar
Reflux ratio (R/D): 13.5
Feed temperature: 36° C.
Reflux temperature: 41° C.
Column head temperature: 51° C.
Column bottom temperature: 55° C.

Table 5 below shows the compositions of the feed and the overhead effluent from the distillation column operating under the conditions described above.

TABLE 5

|  | Feed (weight %) | Head (weight %) |
|---|---|---|
| <$C_4$ | 0.39 | 0.65 |
| $iC_4$ | 6.91 | 13.71 |
| $iC_4^=$ | 82.94 | 84.82 |
| $C_4^=1$ | 0.81 | 0.51 |
| $C_4^{==}1,3$ | — | — |

TABLE 5-continued

| | Feed (weight %) | Head (weight %) |
|---|---|---|
| $nC_4$ | 2.09 | 0.14 |
| $C_4^=2trans$ | 4.44 | 0.12 |
| Neo $C_5$ | — | — |
| Me cyclo $C_3$ | — | — |
| $C_4^=2cis$ | 2.42 | 0.05 |
| $>C_4$ | — | — |

Third Hydroisomerisation

The average operating conditions during the test were as follows:

Reactor temperature: 60° C.
Reactor pressure: 20 bar
residence time: 0.25 to 0.1 h
$H_2$/feed molar ratio: 1

Table 6 below shows the compositions of the feed and effluent in the hydroisomerisation reactor operating under the conditions described above.

TABLE 6

| | Feed (weight %) | Effluent (weight %) |
|---|---|---|
| $<C_4$ | 0.65 | 0.57 |
| $iC_4$ | 13.71 | 14.55 |
| $iC_4^=$ | 84.82 | 84.07 |
| $C_4^=1$ | 0.51 | 0.03 |
| $C_4^{==}1,3$ | — | — |
| $nC_4$ | 0.14 | 0.22 |
| $C_4^=2trans$ | 0.12 | 0.38 |
| Neo $C_5$ | — | — |
| Me cyclo $C_3$ | — | — |
| $C_4^=2cis$ | 0.05 | 0.18 |
| $>C_4$ | — | — |

Third Distillation

Distillation of the effluent from the above test was carried out under the following operating conditions:

Column pressure: 4 bar
Reflux ratio (R/D): 13.5
Feed temperature: 36° C.
Reflux temperature: 41° C.
Column head temperature: 53° C.
Column bottom temperature: 55° C.

Table 7 below shows the compositions of the feed and the overhead effluent from the distillation column operating under the conditions described above.

TABLE 7

| | Feed (weight %) | Head (weight %) |
|---|---|---|
| $<C_4$ | 0.57 | 0.57 |
| $iC_4$ | 14.55 | 14.66 |
| $iC_4^=$ | 84.07 | 84.69 |
| $C_4^=1$ | 0.03 | 0.03 |
| $C_4^{==}1,3$ | — | — |
| $nC_4$ | 0.22 | 0.01 |
| $C_4^=2trans$ | 0.38 | 0.04 |
| Neo $C_5$ | — | — |
| Me cyclo $C_3$ | — | — |
| $C_4^=2cis$ | 0.18 | — |
| $>C_4$ | — | — |

These successive and discontinuous hydroisomerisation and distillation operations represent the separation of 1-butene from isobutene which is carried out continuously in the process of the invention.

Example 4

Pilot hydroisomerisation tests were carried out using a 1-raffinate using the hydroisomerisation catalyst LD267R from PROCATALYSE which packed each of the catalytic beds. The results of these tests are shown in Table 8 below: they allowed computation parameters to be determined which allowed the process of the invention to be simulated using suitable software. The software used for this simulation is sold by SIMCI under the trade name Pro2.

TABLE 8

| pilot test results | | | | | | | | | | | |
|---|---|---|---|---|---|---|---|---|---|---|---|
| T ° C. | | 40 | 80 | 90 | 50 | 50 | 50 | 50 | 50 | 50 | 50 |
| HSV $h^{-1}$ | | 30 | 30 | 30 | 30 | 30 | 30 | 30 | 30 | 20 | 40 |
| P bar | | 10 | 10 | 10 | 6.5 | 10 | 15 | 10 | 10 | 10 | 10 |
| $H_2$/HC m/m | | 0.17 | 0.17 | 0.17 | 0.17 | 0.17 | 0.17 | 0.1 | 0.19 | 0.17 | 0.17 |
| | feed | effl | effl | effl | effl | effl | effl | effl | effl | effl | effl |
| <C4 | 0.14 | 0.11 | 0.12 | 0.11 | 0.10 | 0.10 | 0.10 | 0.10 | 0.11 | 0.10 | 0.09 |
| iC4 | 5.69 | 5.75 | 5.75 | 5.73 | 5.71 | 5.76 | 5.75 | 5.72 | 5.76 | 5.75 | 5.74 |
| iC4= | 78.67 | 78.71 | 78.72 | 78.73 | 78.78 | 78.72 | 78.73 | 78.74 | 78.72 | 78.71 | 78.74 |
| 1-iC4= | 3.66 | 1.30 | 0.91 | 0.75 | 1.15 | 1.01 | 1.18 | 1.13 | 1.00 | 0.8 | 1.32 |
| n-C4 | 7.16 | 7.19 | 7.17 | 7.14 | 7.14 | 7.18 | 7.19 | 7.16 | 7.20 | 7.19 | 7.18 |
| tr2-C4= | 4.36 | 5.40 | 5.48 | 5.40 | 5.46 | 5.49 | 5.41 | 5.46 | 5.48 | 5.59 | 5.37 |
| cs2-C4= | 0.32 | 1.54 | 1.85 | 2.14 | 1.66 | 1.74 | 1.64 | 1.69 | 1.75 | 1.86 | 1.56 | where effl = effluent.

The catalytic hydroisomerising distillation zone comprised 2 or 3 catalytic distillation doublets, each of the doublets being of the type shown in the figure, each doublet being itself constituted by a catalytic cell over which three perforated plates were mounted.

Two examples which were simulated using the calculation were carried out. They are described below.

Example 4A

The configuration of the unit, comprising three catalytic hydroisomerisation beds located inside the column, termed reactive plates, was as follows:

column with 130 theoretical plates, numbered from top to bottom;

supply to plate no. 90;

the reactive plates were plates 10, 25 and 39. Each contained 7.5 m³ of catalyst.

Operating conditions:

Flow rate of liquid supply to column: 292.9 kmole/h;

Reflux ratio: 12;

Column head pressure: 6.2 bars absolute;

Column bottom pressure: 7 bars absolute;

Temperature of supply to column: 59° C.;

Column head temperature: 52° C.;

Column bottom temperature: 64.5° C.;

Temperature of reactive plate no. 10: 53° C.;

Pressure of reactive plate no. 10: 6.6 bars absolute;

Flow rate of liquid traversing reactive plate no. 10: 1660 kmol/h;

Temperature of reactive plate no. 25: 54° C.;

Pressure of reactive plate no. 25: 6.6 bars absolute;

Flow rate of liquid traversing reactive plate no. 25: 1660 kmole/h;

Temperature of reactive plate no. 39: 54° C.;

Pressure of reactive plate no. 39: 6.7 bars absolute;

Flow rate of liquid traversing reactive plate no. 39: 1660 kmole/h.

With this configuration and under those operating conditions, the simulation produced the following results:

|  | Column supply (kmole/h) | Column head (kmole/h) | Column bottom (kmole/h) |
|---|---|---|---|
| <C4 | 1.12 | 1.12 | 0.00 |
| iC4 | 4.46 | 5.58 | 0.00 |
| iC4= | 110.08 | 108.07 | 0.89 |
| C4 = 1 | 7.53 | 0.02 | 0.17 |
| nC4 | 55.27 | 0.13 | 55.23 |
| C4 = 2tr | 79.76 | 0.03 | 84.56 |
| C4 = 2cis | 33.49 | 0.00 | 35.91 |
| H$_2$ | 1.21 | 0.00 | 0.00 |
| Total | 292.92 | 114.95 | 176.76 |

Yield of isobutene at column head: 98.2%

1-butene/isobutene molar ratio at column head: $1.85 \times 10^{-4}$.

Example 4B

The configuration of the unit, comprising two catalytic hydroisomerisation beds located inside the column, termed reactive plates, was as follows:

column with 130 theoretical plates, numbered from top to bottom;

supply to plate no. 90;

the reactive plates were plates 10 and 39. Each contained 7.5 m³ of catalyst.

Operating conditions:

Flow rate of liquid supply to column: 292.9 kmole/h;

Reflux ratio: 12;

Column head pressure: 6.2 bars absolute;

Column bottom pressure: 7 bars absolute;

Temperature of supply to column: 59° C.;

Column head temperature: 52° C.;

Column bottom temperature: 64.5° C.;

Temperature of reactive plate no. 10: 53° C.;

Pressure of reactive plate no. 10: 6.6 bars absolute;

Flow rate of liquid traversing reactive plate no. 10: 1660 kmol/h;

Temperature of reactive plate no. 39: 54° C.;

Pressure of reactive plate no. 39: 6.7 bars absolute;

Flow rate of liquid traversing reactive plate no. 39: 1660 kmole/h.

With this configuration and under those operating conditions, the simulation produced the following results:

|  | Column supply (kmole/h) | Column head (kmole/h) | Column bottom (kmole/h) |
|---|---|---|---|
| <C4 | 1.12 | 1.12 | 0.00 |
| iC4 | 4.46 | 5.17 | 0.00 |
| iC4= | 110.08 | 108.48 | 0.89 |
| C4 = 1 | 7.53 | 0.09 | 0.17 |
| nC4 | 55.27 | 0.13 | 55.20 |
| C4 = 2tr | 79.76 | 0.06 | 84.50 |
| C4 = 2cis | 33.49 | 0.00 | 35.90 |
| H$_2$ | 1.21 | 0.00 | 0.00 |
| Total | 292.92 | 115.49 | 176.66 |

Yield of isobutene at column head: 98.6%

1-butene/isobutene molar ratio at column head: $8.30 \times 10^{-4}$.

The preceding examples can be repeated with similar success by substituting the generically or specifically described reactants and/or operating conditions of this invention for those used in the preceding examples.

The entire disclosures of all applications, patents and publications, cited above and below, and of corresponding application French No. 95/15.530, filed Dec. 27, 1995, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

We claim:

1. A process for the treatment of a feed comprising a major portion of olefinic hydrocarbons containing 4 carbon atoms per molecule, including isobutene, 1-butene and 2-butenes in a ratio which substantially corresponds to the thermodynamic equilibrium, in which said feed is treated in a distillation zone comprising a stripping zone and a rectification zone associated with at least one hydroisomerisation reaction zone, said hydroisomerisation reaction zone being at least partially internal to said distillation zone and comprising at least one catalytic bed, in which hydroisomerisation of at least a portion of 1-butene is carried out in the presence of a hydroisomerisation catalyst and at least one gas stream comprising hydrogen, such that an effluent rich in isobutene leaves the distillation zone overhead and an effluent rich in 2-butenes leaves the bottom, said process being characterized in that each catalytic bed in the internal portion of the hydroisomerisation zone is traversed by an ascending co-current of said gas stream and liquid and is substantially out of contact with the distillation vapor.

2. A process according to claim 1 in which, for each catalytic bed in the internal portion of the reaction zone, the liquid is distributed at a level located below the catalytic bed and the gas stream is distributed at a level below or in the catalytic bed.

3. A process according to claim 2, in which gas is introduced into the liquid upstream of the level where the liquid is distributed with respect to the direction of liquid circulation.

4. A process according to claim 1, in which the gas stream is introduced at a level located substantially at the level of where the liquid is distributed, the gas and liquid being introduced separately into the catalytic bed.

5. A process according to claim 4, in which the gas stream is introduced in the catalytic bed.

6. A process according to claim 4, in which the gas stream is introduced below the catalytic bed.

7. A process according to claim 5, in which the gas stream is introduced at a level located proximate to the level where the liquid is distributed.

8. A process according to claim 1, in which the hydroisomerisation zone is completely internal to the distillation zone.

9. A process according to claim 1, in which the internal portion of the hydroisomerisation zone is at least partially in the rectification zone.

10. A process according to claim 1, in which a major portion of the gas stream is hydrogen.

11. A process according to claim 1, wherein a major portion of 1-butene is subjected to hydroisomerisation.

12. A process according to claim 6, in which the gas stream is introduced at a level located proximate to the level where the liquid is distributed.

* * * * *

UNITED STATES PATENT AND TRADEMARK OFFICE
CERTIFICATE OF CORRECTION

PATENT NO. : 6,054,630
DATED : April 25, 2000
INVENTOR(S): Paul MIKITENKO et al.

It is certified that an error appears in the above-identified patent and that said Letters Patent is hereby corrected as shown below:

```
On the title page:
```

Please correct the information under "Related U.S. Application Data" to read as follows:

--[62] Division of application No. 08/774,841, Dec. 27, 1996, Pat. No. 5,888,355.--.

Signed and Sealed this

Twenty-fourth Day of April, 2001

Attest:

NICHOLAS P. GODICI

Attesting Officer

Acting Director of the United States Patent and Trademark Office